United States Patent
Xie et al.

(10) Patent No.: US 11,053,616 B2
(45) Date of Patent: Jul. 6, 2021

(54) NON-WOVEN ABSORBENT TEXTILE ARTICLE

(71) Applicant: Xiamen Yanjan New Material Co., Ltd., Xiamen (CN)

(72) Inventors: Jihua Xie, Xiamen (CN); Jiquan Xie, Xiamen (CN)

(73) Assignee: Xiamen Yanjan New Material Co., Ltd., Xiamen (CN)

( * ) Notice: Subject to any disclaimer, the term of this patent is extended or adjusted under 35 U.S.C. 154(b) by 476 days.

(21) Appl. No.: 14/905,819

(22) PCT Filed: Jul. 16, 2014

(86) PCT No.: PCT/CN2014/082288
§ 371 (c)(1),
(2) Date: Jan. 17, 2016

(87) PCT Pub. No.: WO2015/007211
PCT Pub. Date: Jan. 22, 2015

(65) Prior Publication Data
US 2016/0153128 A1    Jun. 2, 2016

(30) Foreign Application Priority Data

Jul. 17, 2013  (CN) .......................... 201310301601.1

(51) Int. Cl.
*D04H 1/559* (2012.01)
*D04H 1/4374* (2012.01)
*A61F 13/511* (2006.01)

(52) U.S. Cl.
CPC ....... *D04H 1/559* (2013.01); *A61F 13/51104* (2013.01); *D04H 1/4374* (2013.01); *A61F 2013/51178* (2013.01)

(58) Field of Classification Search
CPC ...... D04H 1/559; D04H 1/4374; D04H 1/541; A61F 13/51104; A61F 13/5123;
(Continued)

(56) References Cited

U.S. PATENT DOCUMENTS 4,883,707 A * 11/1989 Newkirk .................. B32B 5/16
428/219
5,658,639 A *  8/1997 Curro ................ A61F 13/00991
427/243

(Continued)

FOREIGN PATENT DOCUMENTS

CN    1681986 A    10/2005
CN    1723120 A     1/2006
(Continued)

OTHER PUBLICATIONS

First Chinese Office Action cited in Application No. 201310301601.1 dated Mar. 30, 2015, 13 pgs.
(Continued)

*Primary Examiner* — Jennifer A Gillett
(74) *Attorney, Agent, or Firm* — Cooper Legal Group, LLC

(57) ABSTRACT

A nonwoven absorbent textile article for absorbing liquid includes a first fiber layer having perforated through holes with an area of 10-80% based on total area of the first fiber layer, having a thickness ranging from 0.2-2.0 mm, and having a contact angle with water that is larger than 70° to distribute liquid thereon; and a second fiber layer fixedly connected to the first fiber layer in a hot air through oven by heat bonding and having a contact angle with water that is less than 70° to absorb liquid distributed by the first fiber layer, wherein the first fiber layer includes fibers that are sheath/core fibers or an eccentric bi-component fibers, and wherein the first fiber layer has a basis weight of 5-40 g/m² and the second fiber layer has a basis weight of 5-40 g/m².

(Continued)

Contact with the skin of a user has a dryer feel and provides comfort.

6 Claims, 4 Drawing Sheets

(58) Field of Classification Search
CPC ...... A61F 2013/5127; A61F 2013/5128; A61F 2013/51366; A61F 2013/51028; A61F 2013/51178; Y10T 428/24331; Y10T 442/637; Y10T 442/638; Y10T 442/641; Y10T 442/659; Y10T 442/692
USPC ........ 442/361, 362, 364, 381, 411; 428/138, 428/131, 134, 137
See application file for complete search history.

(56) References Cited

U.S. PATENT DOCUMENTS

| | | | | |
|---|---|---|---|---|
| 5,752,945 | A * | 5/1998 | Mosley | A61F 13/53747 604/370 |
| 5,989,688 | A * | 11/1999 | Barge | D04H 3/14 156/285 |
| 6,168,849 | B1 * | 1/2001 | Braverman | A61F 13/15731 428/137 |
| 6,461,716 | B1 * | 10/2002 | Lee | A61F 13/512 428/132 |
| 7,005,558 | B1 * | 2/2006 | Johansson | A61F 13/512 604/370 |
| 7,507,463 | B2 * | 3/2009 | Noda | D04H 1/74 428/131 |
| 2002/0107495 | A1 * | 8/2002 | Chen | A61F 13/512 604/365 |
| 2004/0087924 | A1 * | 5/2004 | Sroda | A61F 13/47209 604/367 |
| 2007/0015428 | A1 * | 1/2007 | Ishikawa | B32B 5/26 442/409 |
| 2009/0247977 | A1 * | 10/2009 | Takeuchi | A61F 13/511 604/375 |

FOREIGN PATENT DOCUMENTS

| | | | |
|---|---|---|---|
| CN | 101554487 A | 10/2009 | |
| CN | 102257201 A | 11/2011 | |
| CN | 102673030 A | 9/2012 | |
| CN | 102753129 A | 10/2012 | |
| CN | 202637294 U | 1/2013 | |
| CN | 103422256 A | 12/2013 | |
| CN | 203393410 U | 1/2014 | |
| JP | 2005-324010 A | 11/2005 | |
| JP | 2009279097 A | 12/2009 | |
| JP | 2009279098 A | 12/2009 | |
| JP | 2011135979 A | 7/2011 | |
| JP | 2012005744 A | 1/2012 | |
| JP | 2012143543 A | 8/2012 | |
| WO | WO-2010032951 A2 * | 3/2010 | ............... D04H 1/74 |
| WO | 2010/074207 A1 | 7/2010 | |

OTHER PUBLICATIONS

Second Chinese Office Action cited in Application No. 201310301601.1 dated Nov. 18, 2015, 15 pgs.
First Japanese Office Action cited in Application No. 2016-526432 dated Feb. 7, 2017, 10 pgs.
Second Japanese Office Action cited in Application No. 2016-526432 dated Sep. 12, 2017, 10 pgs.
Third Japanese Office Action cited in Application No. 2016-526432 dated Jun. 12, 2018, 7 pgs.
First Korean Office Action cited in Application No. 10-2016-7001803 dated Sep. 15, 2017, 13 pgs.
Second Korean Office Action cited in Application No. 10-2016-7001803 dated Jan. 31, 2018, 6 pgs.
Third Korean Office Action cited in Application No. 10-2016-7001803 dated May 2, 2018, 11 pgs.

* cited by examiner

NON-WOVEN ABSORBENT TEXTILE ARTICLE

BACKGROUND OF THE INVENTION

1. Field of the Invention

The present invention relates to the field of absorbent textiles, especially to a hot air through nonwoven fabric and the manufacturing method thereof.

2. Background of the Related Art

Nonwoven fabric is widely used in the hygienic products, cleaning products and medical products, etc., like sanitary napkins, paper diapers, wipes and masks and so on. Existing nonwoven has the surface contacted with the skin of the user with convex-concave structure made by embossing process, this kind of structure can reduce the contact area with the skin of the wearer, so as to reduce adhesiveness feeling or mismatch. However, this kind of nonwoven is mostly applied hydrophilic fiber as the raw material, which is although benefit to absorb the liquid of the surface quickly, it has higher surface energy that the liquid is easily absorbed around the fiber, some liquid residuals between the fibers, at the same time, the capillary phenomenon of the fiber will make the absorbed liquid back to the surface of the nonwoven, the user would feel moist, stick and wet. Besides, the nonwoven is made to be the surface layer of the paper diapers for babies, as it has bad dry performance, it may result in hypersensitivity like reddening of skin and eczema.

SUMMARY OF THE INVENTION

The present invention provides a hot air through nonwoven to overcome the disadvantages of the existing known technology.

The technical proposal of the present invention is that:

A hot air through nonwoven, comprising a first fiber layer and a second fiber layer that are fixedly connected up and down; the contact angle of the first fiber layer and water is larger than 70.degree., the thickness of the first fiber layer is 0.2-2.0 mm, the first fiber layer has throughout holes, the area of the throughout holes has 10-80% of the total area of the first fiber layer; the contact angle of the second fiber layer and water is less than 70.degree.; the first fiber layer is used to distribute the liquid thereon to the second fiber layer, the second fiber layer is used to absorb the liquid from the first fiber layer.

In another preferred embodiment, the throughout holes are throughout holes of strip, circle, ellipse, polygon or other irregular shape and arranged with space, or protrusions of strip, circle, ellipse, polygon or other irregular shape.

In another preferred embodiment, the first fiber layer has two layers or more.

In another preferred embodiment, the fiber of the first fiber layer is sheath/core or eccentric bi-component fiber.

In another preferred embodiment, the second fiber layer has two layers or more.

In another preferred embodiment, the basis weight of the first fiber layer is 5-40 g/m2, the basis weight of the second fiber layer is 5-40 g/m2.

Another technical proposal of the present invention is that:

A manufacturing method of the hot air through nonwoven according to claim 1, comprising following steps:

(1) the fiber for the first fiber layer is carded by the carding machine to form the first fiber layer, the thickness of the first fiber layer is 0.2-2.0 mm, the basis weight is 5-40 g/m2;

(2) the first fiber layer is made throughout holes by perforating process, the area of the throughout holes is 10-80% of the total area of the first fiber layer, the throughout holes are throughout holes of strip, circle, ellipse, polygon or other irregular shape and arranged with space, or protrusions of strip, circle, ellipse, polygon or other irregular shape;

(3) the fiber for the second fiber layer is carded by the carding machine to form the second fiber layer, the basis weight is 5-40 g/m2;

(4) the obtained first fiber layer and the second fiber layer are overlaid and sent to a hot air through oven for heat bonding to form the hot air through nonwoven.

In another preferred embodiment, the first fiber layer has two layers or more.

In another preferred embodiment, the fiber of the first fiber layer is sheath/core or eccentric bi-component fiber.

In another preferred embodiment, the second fiber layer has two layers or more.

The present invention has advantages as follows:

1. The hot air through nonwoven of the present invention comprises a first fiber layer and a second fiber layer that are fixedly connected up and down; the contact angle of the first fiber layer and water is larger than 70.degree., the contact angle of the second fiber layer and water is less than 70.degree.; the first fiber layer has throughout holes, the area of the throughout holes has 10-80% of the total area of the first fiber layer; the throughout holes are throughout holes of strip, circle, ellipse, polygon or other irregular shape and arranged with space, or protrusions of strip, circle, ellipse, polygon or other irregular shape; when the body fluid reaches to the first fiber layer, which has low surface energy, it then flows to the second fiber layer through the throughout holes of the first fiber layer, so that it not only has distributing function, but also enlargers the diffusing area, thus increasing the effective use area of the absorbent product and improving the absorbent performance of the liquid; as the second fiber layer has higher surface energy, when the body fluid reaches to the second fiber layer, it is quickly absorbed into the layer; at the same time, as the contact angle of the first fiber layer and water is larger than 70.degree., it prevents the absorbed body fluid from moving back to the surface of the absorbent product, achieving dry and comfortable effect; as the thickness of the first fiber layer is larger than 0.2 mm, even the body fluid effuses the second fiber layer, only the first fiber layer contacts with the skin of the user, the user would not feel wet.

2. The manufacturing method of the present invention is simple, it requests low to the equipment that it is applicable in industrial manufacture.

DETAILED DESCRIPTION OF THE INVENTION

The present invention will be further described with the embodiments.

The First Embodiment

Figure 1:
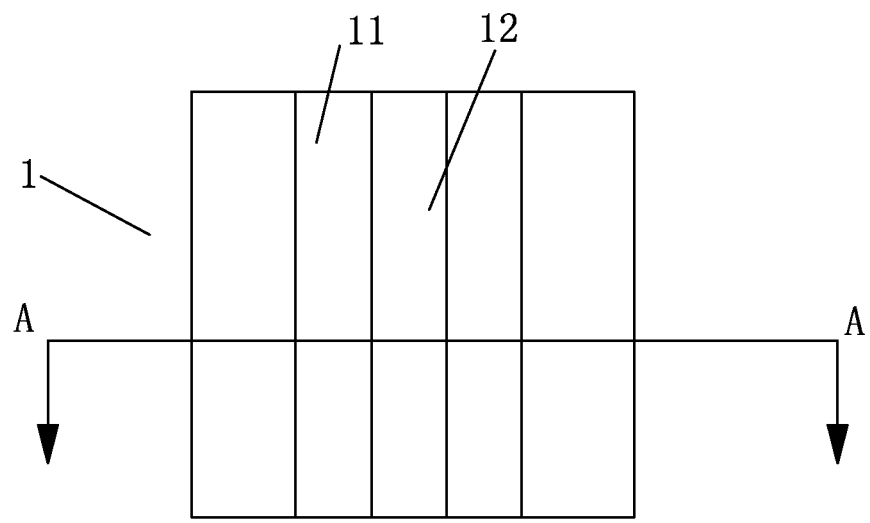
FIG. 1 illustrates a top view of a solid nonwoven of a first embodiment of the present invention.
Figure 2:
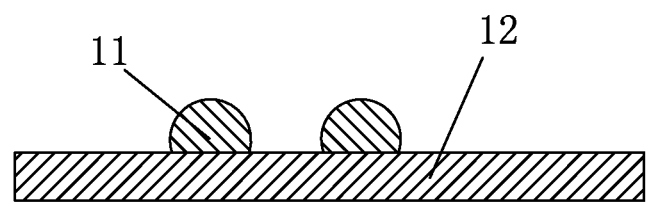
FIG. 2 illustrates a sectional diagram of the nonwoven of FIG. 1 in A-A.

As figured in FIG. 1 and FIG. 2, a hot air through nonwoven 1 comprises a first fiber layer 11 and a second fiber layer 12 that are fixedly connected up and down; the contact angle of the first fiber layer 11 and water is larger than 70.degree., the contact angle of the second fiber layer and water is less than 70.degree.; the first fiber layer 11 is used to distribute the liquid thereon to the second fiber layer 12, the second fiber layer 12 is used to absorb the liquid from the first fiber layer 11; the first fiber layer 11 has throughout holes, the area of the throughout holes has 10-80% of the total area of the first fiber layer 11, the throughout holes are parallel strip protrusions; the fiber of the first fiber layer is sheath/core or eccentric bi-component fiber.

The thickness of the first fiber layer 11 is 0.2-2.0 mm,

The basis weight of the first fiber layer is 5-40 g/m2, preferred 5-20 g/m2.

The basis weight of the second fiber layer is 5-40 g/m2, preferred 5-20 g/m2.

The manufacturing method of the hot air through nonwoven 1 of this embodiment comprises following steps:

(1) the fiber for the first fiber layer 11 is carded by the carding machine to form the first fiber layer 11;

(2) the first fiber layer 11 is made parallel strip protrusions by a perforating device;

(3) the fiber for the second fiber layer 12 is carded by the carding machine to form the second fiber layer 12;

(4) the obtained first fiber layer 11 and the second fiber layer 12 are overlaid and sent to a hot air through oven for heat bonding to form the hot air through nonwoven 1.

The Second Embodiment

Figure 3:
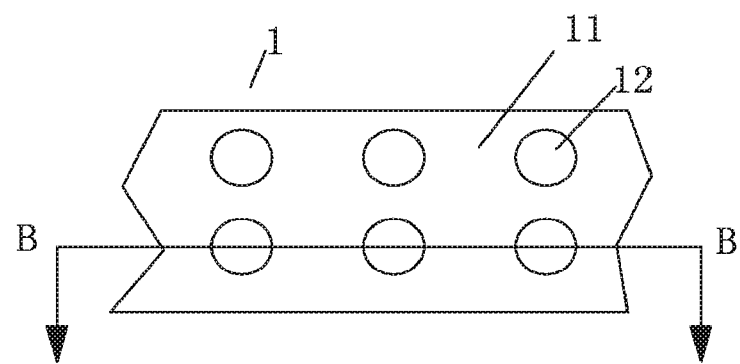
FIG. 3 illustrates a top view of a solid nonwoven of a second embodiment of the present invention.
Figure 4:
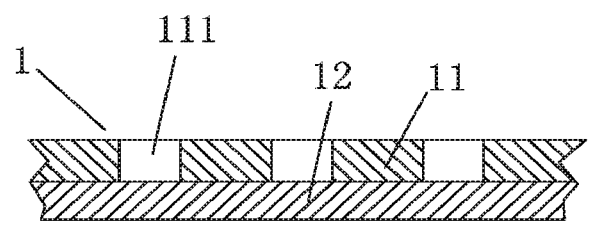
FIG. 4 illustrates a sectional diagram of the nonwoven of FIG. 3 in B-B.

As figured in FIG. 3 and FIG. 4, a hot air through nonwoven 1 comprises a first fiber layer 11 and a second fiber layer 12 that are fixedly connected up and down; the contact angle of the first fiber layer 11 and water is larger than 70.degree., the contact angle of the second fiber layer and water is less than 70.degree.; the first fiber layer 11 is used to distribute the liquid thereon to the second fiber layer 12, the second fiber layer 12 is used to absorb the liquid from the first fiber layer 11; the first fiber layer 11 has throughout holes, the area of the throughout holes has 10-80% of the total area of the first fiber layer 11, the throughout holes are circle throughout holes 111 arranged with space; the fiber of the first fiber layer is double-component fiber of skin-core structure or eccentric structure.

The thickness of the first fiber layer 11 is 0.2-2.0 mm,

The basis weight of the first fiber layer is 5-40 g/m2, preferred 5-20 g/m2.

The basis weight of the second fiber layer is 5-40 g/m2, preferred 5-20 g/m2.

The manufacturing method of the hot air through nonwoven 1 of this embodiment comprises following steps:

(1) the fiber for the first fiber layer 11 is carded by the carding machine to form the first fiber layer 11;

(2) the first fiber layer 11 is made circle throughout holes 111 arranged with space by a perforating device;

(3) the fiber for the second fiber layer 12 is carded by the carding machine to form the second fiber layer 12;

(4) the obtained first fiber layer 11 and the second fiber layer 12 are overlaid and sent to a hot air through oven for heat bonding to form the hot air through nonwoven 1.

The Third Embodiment

Figure 5:
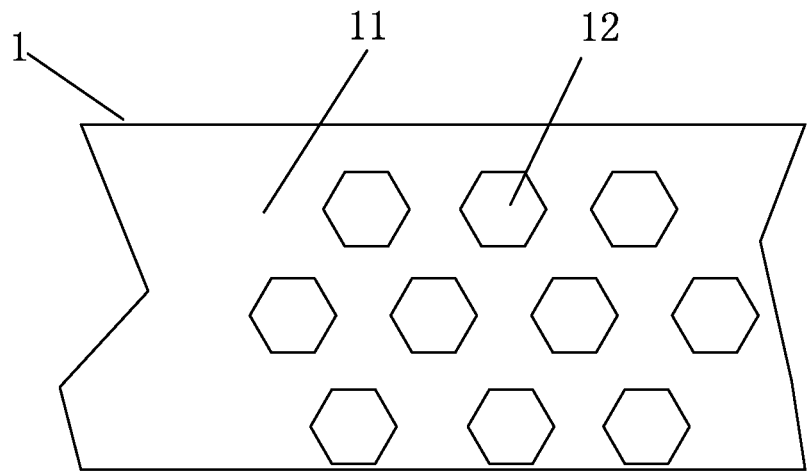
FIG. 5 illustrates a top view of a solid nonwoven of a third embodiment of the present invention.

As figured in FIG. 5, a hot air through nonwoven 1 comprises a first fiber layer 11 and a second fiber layer 12 that are fixedly connected up and down; the contact angle of the first fiber layer 11 and water is larger than 70.degree., the contact angle of the second fiber layer and water is less than 70.degree.; the first fiber layer 11 is used to distribute the liquid thereon to the second fiber layer 12, the second fiber layer 12 is used to absorb the liquid from the first fiber layer 11; the first fiber layer 11 has throughout holes, the area of the throughout holes has 10-80% of the total area of the first fiber layer 11, the throughout holes are polygon protrusions arranged with space; the fiber of the first fiber layer is sheath/core or eccentric bi-component fiber.

The thickness of the first fiber layer 11 is 0.2-2.0 mm,

The basis weight of the first fiber layer is 5-40 g/m2, preferred 5-20 g/m2.

The basis weight of the second fiber layer is 5-40 g/m2, preferred 5-20 g/m2.

The manufacturing method of the hot air through nonwoven 1 of this embodiment comprises following steps:

(1) the fiber for the first fiber layer 11 is carded by the carding machine to form the first fiber layer 11;

(2) the first fiber layer 11 is made polygon protrusions arranged with space by a perforating device;

(3) the fiber for the second fiber layer 12 is carded by the carding machine to form the second fiber layer 12;

(4) the obtained first fiber layer 11 and the second fiber layer 12 are overlaid and sent to a hot air through oven for heat bonding to form the hot air through nonwoven 1.

The Fourth Embodiment

Figure 6:
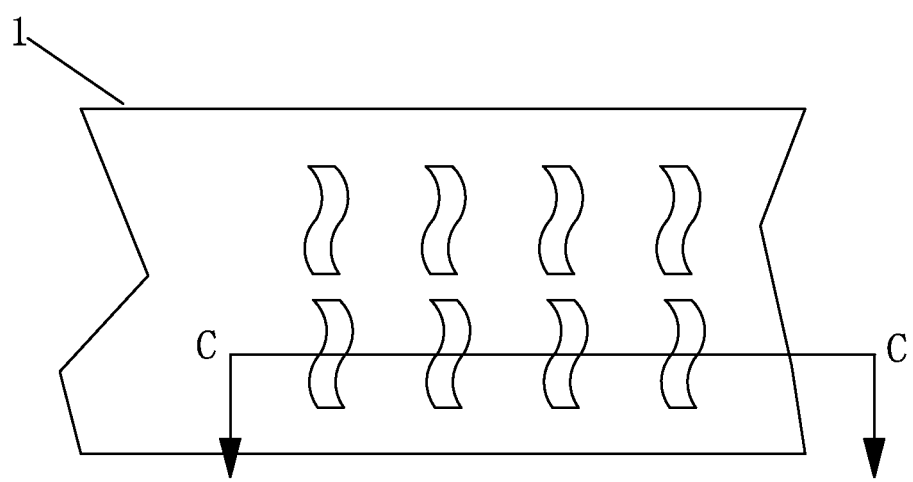
FIG. 6 illustrates a top view of a solid nonwoven of a forth embodiment of the present invention.
Figure 7:
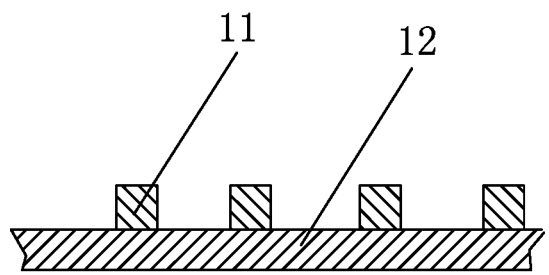
FIG. 7 illustrates a sectional diagram of the nonwoven of FIG. 6 in C-C.

As figured in FIG. 6 and FIG. 7, a hot air through nonwoven 1 comprises a first fiber layer 11 and a second fiber layer 12 that are fixedly connected up and down; the contact angle of the first fiber layer 11 and water is larger than 70.degree., the contact angle of the second fiber layer and water is less than 70.degree.; the first fiber layer 11 is used to distribute the liquid thereon to the second fiber layer 12, the second fiber layer 12 is used to absorb the liquid from the first fiber layer 11; the first fiber layer 11 has throughout holes, the area of the throughout holes has 10-80% of the total area of the first fiber layer 11, the throughout holes are short bar protrusions of irregular shaped arranged with space; the fiber of the first fiber layer is sheath/core or eccentric bi-component fiber.

The thickness of the first fiber layer 11 is 0.2-2.0 mm,

The basis weight of the first fiber layer is 5-40 g/m2, preferred 5-20 g/m2.

The basis weight of the second fiber layer is 5-40 g/m2, preferred 5-20 g/m2.

The manufacturing method of the hot air through nonwoven 1 of this embodiment comprises following steps:

(1) the fiber for the first fiber layer 11 is carded by the carding machine to form the first fiber layer 11;

(2) the first fiber layer 11 is made short bar protrusions of irregular shaped arranged with space by a perforating device;

(3) the fiber for the second fiber layer 12 is carded by the carding machine to form the second fiber layer 12;

(4) the obtained first fiber layer 11 and the second fiber layer 12 are overlaid and sent to a hot air through oven for heat bonding to form the hot air through nonwoven 1.

The Fifth Embodiment

Figure 8:
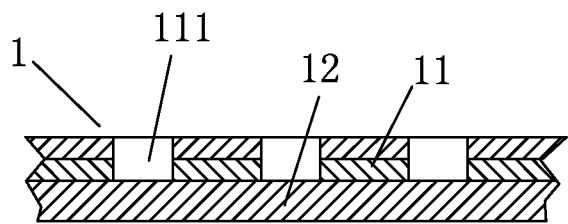
FIG. 8 illustrates a sectional diagram of a solid nonwoven of a fifth embodiment of the present invention.
Figure 9:
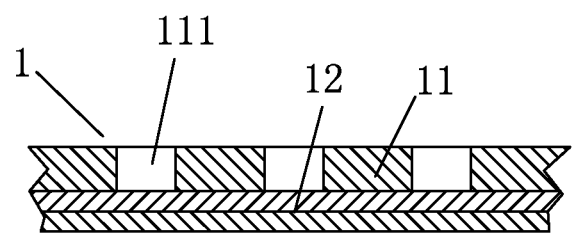
FIG. 9 illustrates a sectional diagram of a solid nonwoven of a sixth embodiment of the present invention.

As figured in FIG. 8, a hot air through nonwoven 1 comprises a first fiber layer 11 and a second fiber layer 12 that are fixedly connected up and down; the contact angle of the first fiber layer 11 and water is larger than 70.degree., the contact angle of the second fiber layer and water is less than 70.degree.; the first fiber layer 11 is used to distribute the liquid thereon to the second fiber layer 12, the second fiber layer 12 is used to absorb the liquid from the first fiber layer 11; the first fiber layer 11 has throughout holes, the area of the throughout holes has 10-80% of the total area of the first fiber layer 11, the throughout holes are circle, ellipse, polygon or irregular shape throughout holes 111 arranged with space; the fiber of the first fiber layer is sheath/core or eccentric bi-component fiber. The first fiber layer 11 has double layers.

The thickness of the first fiber layer 11 is 0.2-2.0 mm,

The basis weight of the first fiber layer is 5-40 g/m2, preferred 5-20 g/m2.

The basis weight of the second fiber layer is 5-40 g/m2, preferred 5-20 g/m2.

The manufacturing method of the hot air through nonwoven 1 of this embodiment comprises following steps:

(1) the fiber for the first fiber layer 11 is carded by the carding machine to form the first fiber layer 11;

(2) the first fiber layer 11 is made circle, ellipse, polygon or irregular shape throughout holes 111 arranged with space by a perforating device;

(3) the fiber for the second fiber layer 12 is carded by the carding machine to form the second fiber layer 12;

(4) the obtained first fiber layer 11 and the second fiber layer 12 are overlaid and sent to a hot air through oven for heat bonding to form the hot air through nonwoven 1.

The Sixth Embodiment

As figured in FIG. 8, a hot air through nonwoven 1 comprises a first fiber layer 11 and a second fiber layer 12 that are fixedly connected up and down; the contact angle of the first fiber layer 11 and water is larger than 70.degree., the contact angle of the second fiber layer and water is less than 70.degree.; the first fiber layer 11 is used to distribute the liquid thereon to the second fiber layer 12, the second fiber layer 12 is used to absorb the liquid from the first fiber layer 11; the first fiber layer 11 has throughout holes, the area of the throughout holes has 10-80% of the total area of the first fiber layer 11, the throughout holes are circle, ellipse, polygon or irregular shape throughout holes 111 arranged with space; the fiber of the first fiber layer is sheath/core or eccentric bi-component fiber. The second fiber layer 12 has double layers.

The thickness of the first fiber layer 11 is 0.2-2.0 mm,

The basis weight of the first fiber layer is 5-40 g/m2, preferred 5-20 g/m2.

The basis weight of the second fiber layer is 5-40 g/m2, preferred 5-20 g/m2.

The manufacturing method of the hot air through nonwoven 1 of this embodiment comprises following steps:

(1) the fiber for the first fiber layer 11 is carded by the carding machine to form the first fiber layer 11;

(2) the first fiber layer 11 is made circle, ellipse, polygon or irregular shape throughout holes 111 arranged with space by a perforating device;

(3) the fiber for the second fiber layer 12 is carded by the carding machine to form the second fiber layer 12;

(4) the obtained first fiber layer 11 and the second fiber layer 12 are overlaid and sent to a hot air through oven for heat bonding to form the hot air through nonwoven 1.

Although the present invention has been described with reference to the preferred embodiments thereof for carrying out the patent for invention, it is apparent to those skilled in the art that a variety of modifications and changes may be made without departing from the scope of the patent for invention which is intended to be defined by the appended claims.

INDUSTRIAL APPLICABILITY

When the body fluid reaches the first fiber layer, which has low surface energy, it then flows to the second fiber layer through the through holes of the first fiber layer, so that it not only has a distributing function, but also enlarges the diffusing area, thus increasing the effective use area of the absorbent product and improving the absorbent performance on the liquid; as the second fiber layer has higher surface energy, so that when the body fluid reaches the second fiber layer, it is quickly absorbed into the layer.

The invention claimed is:

1. A nonwoven absorbent textile article for absorbing liquid, comprising:
   a first fiber layer having perforated through holes, having a thickness ranging from 0.2-2.0 mm, and having a contact angle with water that is larger than 70° to distribute liquid thereon; and
   a second fiber layer having a contact angle with water that is less than 70° to absorb liquid distributed by the first fiber layer, wherein:
      the first fiber layer has a basic weight of 5-40 g/m$^2$ and the second fiber layer has a basic weight of 5-40 g/m$^2$,
      the second fiber layer extends continuously and uninterruptedly between two ends of the second fiber layer, and
      the nonwoven absorbent textile article is manufactured according to the following steps:
         (1) first fibers for the first fiber layer are carded by a carding machine to form the first fiber layer,
         (2) the perforated through holes are made by a perforating process, an area of the perforated through holes is 10-80% of a total area of the first fiber layer,
         (3) second fibers for the second fiber layer are carded by the carding machine to form the second fiber layer, and
         (4) the first fiber layer and the second fiber layer are overlaid and sent to a hot air through oven for heat bonding to form the nonwoven absorbent textile article.

2. The nonwoven absorbent textile article according to claim 1, wherein the perforated through holes are spaced apart and have a shape selected from the group consisting of a strip, a circle, an ellipse, and a polygon.

3. The nonwoven absorbent textile article according to claim 1, wherein the first fiber layer comprises a plurality of layers.

4. The nonwoven absorbent textile article according to claim 1, wherein the second fiber layer comprises a plurality of layers.

5. The nonwoven absorbent textile article according to claim 1, wherein the first fibers comprises sheath/core fibers.

6. The nonwoven absorbent textile article according to claim 1, wherein the first fibers comprises eccentric bi-component fibers.

* * * * *